(12) United States Patent
Varkuti

(10) Patent No.: US 10,249,041 B2
(45) Date of Patent: Apr. 2, 2019

(54) ADAPTATION OF IMAGE DATA SETS TO AN UPDATED ATLAS-BASED REFERENCE SYSTEM

(71) Applicant: Brainlab AG, Munich (DE)

(72) Inventor: Balint Varkuti, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/547,723

(22) PCT Filed: Feb. 26, 2015

(86) PCT No.: PCT/EP2015/054030
§ 371 (c)(1),
(2) Date: Jul. 31, 2017

(87) PCT Pub. No.: WO2016/134771
PCT Pub. Date: Sep. 1, 2016

(65) Prior Publication Data
US 2018/0012358 A1    Jan. 11, 2018

(51) Int. Cl.
*G06K 7/00* (2006.01)
*G06T 7/00* (2017.01)
(Continued)

(52) U.S. Cl.
CPC ............ *G06T 7/0014* (2013.01); *G06F 16/58* (2019.01); *G06F 19/321* (2013.01); *G06T 5/50* (2013.01);
(Continued)

(58) Field of Classification Search
CPC ...... G06F 19/321; G06F 19/00; G06F 19/324; G06F 19/345; G06F 19/3406;
(Continued)

(56) References Cited

U.S. PATENT DOCUMENTS 6,246,901 B1 * 6/2001 Benaron ............. A61B 5/0071
600/407
7,720,520 B2 * 5/2010 Willis ................. A61B 5/0422
111/111
(Continued)

FOREIGN PATENT DOCUMENTS

WO    WO2007037848 A2    4/2007

OTHER PUBLICATIONS

International Search Report and Written Opinion for PCT/EP2015/054030 dated Jan. 12, 2015.

*Primary Examiner* — Aklilu K Woldemariam
(74) *Attorney, Agent, or Firm* — Middleton Reutlinger

(57) ABSTRACT

The invention relates to a computer-implemented medical data processing method for determining a mapping of medical image content into a reference system, the method comprising executing, on a processor of a computer, steps of: a) acquiring, at the processor, medical image data describing a digital medical image of an anatomical structure of a patient's body; b) acquiring, at the processor, image attribute data describing attribute information associated with the medical image data, the attribute information including an indication of an initial reference system in which spatial relationships of the digital medical image are defined; c) acquiring, at the processor, reference system transformation data describing a spatial relationship (REG) between the initial reference system and a second reference system which is different from the initial reference system; d) determining, by the processor and based on the medical image data and the reference system transformation data, transformed image data describing a representation of the digital medical image in the second reference system.

13 Claims, 3 Drawing Sheets

(51) Int. Cl.
*G06F 16/58* (2019.01)
*G06T 7/30* (2017.01)
*G06F 19/00* (2018.01)
*G06T 5/50* (2006.01)
*G06T 7/10* (2017.01)

(52) U.S. Cl.
CPC .................. *G06T 7/30* (2017.01); *G06T 7/10* (2017.01); *G06T 2207/20128* (2013.01); *G06T 2207/20221* (2013.01); *G06T 2207/30016* (2013.01)

(58) Field of Classification Search
CPC ..... G06F 17/30265; G06T 2207/10081; G06T 2207/10104; G06T 2207/10088; G06T 2207/20101; G06T 2207/30004; G06T 7/0012; G06T 7/0024; G06T 7/30; G06T 7/401; G06T 7/41; G06T 7/344; G06T 2207/10072; G06T 2207/20221; G06T 2200/04; G06T 2207/10084; G06T 2207/10116; G06T 2207/10132; G06T 2207/10136; G06T 2207/20128; G06T 2207/30016; G06T 2207/30056; G06T 2207/30101; G06T 3/0068; G06T 5/50; G06T 7/0014; G06T 7/10; G06T 7/11; G06T 7/136; G06T 7/143; G06T 7/187; G06T 7/33; G06T 7/38; G06Q 50/22; G16H 50/20; G16H 40/63; A61B 5/0013; A61B 5/0035; A61B 5/055; A61B 5/7246; A61B 6/032; A61B 6/037; A61B 6/5235; A61B 19/52; A61B 2019/5289; A61B 6/584; A61B 6/12; A61B 34/20; A61B 6/5247; A61B 90/36; A61B 2034/2051; A61B 2090/372; A61B 2090/378; A61B 2090/3929; A61B 2090/504; A61B 2090/508; A61B 5/0422; A61B 5/743; A61B 6/4405; A61B 6/462; A61B 6/463; A61B 6/467; A61B 6/487; A61B 6/503; A61B 6/547; A61B 8/00; A61B 8/0833; A61B 8/0841; A61B 8/0883; A61B 8/463; A61B 8/5238; 90/50; A61B 17/320068; A61B 2017/00106; A61B 2034/101; A61B 2034/2048; A61B 2034/2055; A61B 2090/374; A61B 2562/0238; A61B 5/0071; A61B 5/0073; A61B 5/0075; A61B 5/0084; A61B 5/0091; A61B 5/1455; A61B 5/415; A61B 5/418; A61B 5/4381; A61B 5/6848; A61B 6/5264; A61B 8/0858; A61B 8/5261; A61B 90/37; A61B 2090/364; A61N 2005/1058; A61N 2005/1061; A61N 5/1049; A61N 5/1065; A61N 7/02; G06K 9/6206; G06K 2209/05; G06K 9/32; G06K 9/4604; G06K 9/6201; F04C 2270/041; B82Y 10/00; B82Y 20/00; B82Y 5/00; G01N 33/57415; G01N 33/57434; Y10S 977/869; Y10S 977/904
USPC ........ 382/128, 129, 130, 131, 132; 600/407, 600/424
See application file for complete search history.

(56) References Cited

U.S. PATENT DOCUMENTS

| | | | |
|---|---|---|---|
| 8,588,495 B2 | 11/2013 | Gupta et al. | |
| 2003/0194057 A1* | 10/2003 | Dewaele | G06T 7/0012 378/210 |
| 2006/0116575 A1* | 6/2006 | Willis | A61B 5/0422 600/434 |
| 2007/0038058 A1 | 2/2007 | West et al. | |
| 2008/0175463 A1* | 7/2008 | Strommer | G06K 9/32 382/131 |
| 2009/0226060 A1* | 9/2009 | Gering | G06T 7/11 382/128 |
| 2010/0128953 A1* | 5/2010 | Ostrovsky-Berman | G06T 7/35 382/131 |
| 2010/0142774 A1* | 6/2010 | Ben-Haim | G06F 19/321 382/128 |
| 2012/0041779 A1 | 2/2012 | Boroczky et al. | |
| 2013/0072787 A1* | 3/2013 | Wallace | A61B 6/12 600/424 |
| 2013/0177224 A1 | 7/2013 | Papageorgiou et al. | |
| 2014/0148690 A1* | 5/2014 | Kim | A61B 6/5264 600/424 |
| 2015/0065859 A1* | 3/2015 | Hwang | A61B 8/5261 600/411 |
| 2015/0126799 A1* | 5/2015 | Vahala | A61N 5/1049 600/1 |
| 2016/0104287 A1* | 4/2016 | Ryu | A61B 90/37 382/131 |

* cited by examiner

ADAPTATION OF IMAGE DATA SETS TO AN UPDATED ATLAS-BASED REFERENCE SYSTEM

The present invention is directed to a computer-implemented medical data processing method for determining a mapping of medical image content into a reference system, a non-transitory computer-readable program storage medium storing such a program, a computer running that program or comprising that program storage medium, and a system comprising that computer.

In order to aggregate spatial information across patients from patient-specific medical image data, each image containing such information (e.g. segmented objects, landmarks, trajectories) needs to be mapped onto a comparison, for example a common space—usually an, for example a brain atlas such as the Universal Atlas supplied by Brainlab AG. At the same time, applying knowledge gathered in said common space to an individual patient requires the transfer and deformation/adaptation of contents from the common space (e.g. segmentations) into the individual patient image. Utilization of the known spatial relationship between a common space and an individual patient image (henceforth also referred to as the "registration" or a transformation between reference systems) in a bidirectional manner (individual to common space and back) lies at the heart of such information gather and re-application.

However, with changing versions of atlases (the common space), registration methods (applied to the patient-specific medical images and the common space to establish the spatial relationship of the patient-specific medical images to the common space the common space to generate their registration) and access rights to said information, it is very challenging to keep the flow of information valid and comparable (and small footprint in terms of data storage space) in a decentralized data environment which cannot be synchronised regularly. An example of such an environment is the platform universe of devices supplied by Brainlab AG which can be connected to the internet directly (e.g. a workstation with a Quentry® installation), to a hospital network and picture archiving and communication System (PACS—such as one running on e.g. a Buzz®) or not connected to any other device directly at all (such as an image-guided surgery system, e.g. a CURVE® receiving data only via USB stick transfer) or only intermittently (such as the same CURVE® being connected to the local network from time to time).

The issues to be discussed can be further explained as follows:

A single image can contain "content", which is information (usually spatially located in one location of said patient's body) that is generated or recognizable in the medical images of the patient directly. Example could be the segmentation of a tumour object, the orientation of a trajectory depicting the orientation of a lead or screw implant, the identification of a point in space as a landmark (such as e.g. the anterior commissure). Irrespective of the presence of content, patient images are usually automatically registered to produce the registration in order to establish a mapping of the patients anatomy onto a common space and vice versa. This relationship is at the core of any automatic segmentation of anatomy in the patient images.

As soon as the Registration is established, content originating from (and associated with) the patient-specific medical image (hereinforth also abbreviated as Content_Pat) can be transferred via the Registration into a common or comparison space (hereinforth also abbreviated as Content_Com). Such a common space is usually one version of a brain atlas but could as well be one individual dataset regarded as a default patient etc. As each version of an atlas produces one Common Space for comparison and each Content_Pat has to pass through a Registration manufactured by one particular version of a registration engine (theoretically registration method and atlas can develop independently of one another, however in practice they are often versioned in parallel), each entity of Content_Com should have the attributes: version of Common Space, version of registration engine applied and (since theoretically probabilistic methods can yield multiple result of a Registration upon re-run) a unique version of the Registration.

Aggregations of such content can occur on a local, group or central level. For example a system can be installed on one local (unconnected) platform that produces registrations for all patient images on that system, creates the respective Content_Com from the Content_Pat and aggregates the information locally into e.g. an average (an example of a result). That result (e.g. the average location of the spleens of all patients on that system) is unique for the number of Content_Com (e.g. segmented spleens mapped into the common space via the respective registrations) processed by one act of aggregation. Such aggregations are governed by semantic rules to avoid comparing apples with oranges, such as in this example "If there is a segmentation of a spleen, take all that can be found and average them in atlas space". However one single entity or group of identical Content_Com can be utilized by multiple aggregations following different semantics (e.g. "average all spleens" or "look at spleens segmented in the same patient over time and compare their volume with the progression of treatment").

The aforementioned result can now be applied to an individual patient by transferring the result (e.g. an average segmentation volume of spleens) back via the registration into the individual patient image—creating Content_Res (located in patient space) as the result of processing Content_Com (Content_Rest can thus be embodied by a statistical map of certain targets). The result can be compared with the Content_Pat in that patient and the comparison can have diagnostic value and/or provide clinical division support (e.g. "that individual patient's spleen has a lower/higher volume than the average of all I've treated on this system"). Examples of Content_Res are segmentation objects (best average location of the spleen), (statistical) maps (a colour depiction of a spatial summation of all known locations of screws placed), trajectories (the average trajectory used to target the subthalamic nucleus in deep brain stimulation surgery), landmarks (the best practice first incision point on the skin) or similar. While on a local level this works well, on a group or central level (the connection of multiple local data sources) there has to be agreement on which version of the Common Space and registration engine to use, so that multiple entities Content_Pat originating out of multiple local data sources/systems can be compared in one identical group-level Common Space. Since it is operationally not feasible and unrealistic to have forced top-down updates of local versions of Common Space and registration engines across all local systems (especially since they are decentralized in the sense that there is currently no central synchronising mechanism) strategies have to be in place to deal with an aggregation of Contents on a group or central level, with Contents originating from a heterogenic data environment.

For the sake of completeness, one should understand that the system that applies a registration can be versioned as well and constitute an aspect of the (bidirectional) registration engine.

An object of the invention therefore is to provide a method for adapting the registration if it becomes invalid, the for example in case the atlas version changes, thereby spatial providing a changed common space having e.g. changed positions of anatomical structures.

Aspects of the present invention, examples and exemplary steps and their embodiments are disclosed in the following. Different advantageous features can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The present invention relates for example to a method of mapping a digital medical image into a different reference system (a different coordinate system) to keep it comparable to other digital medical images if all digital medical images are defined in a common reference system such as an atlas, in case the common reference system (the atlas) is updated. In order to do so, a transformation is applied to map the digital medical image into the updated reference system.

GENERAL DESCRIPTION OF THE PRESENT INVENTION

In this section, a description of the general features of the present invention is given for example by referring to possible embodiments of the invention.

In one aspect, the invention is directed to a computer-implemented medical data processing method for determining a mapping of medical image content into a reference system.

The method comprises the following exemplary steps which are (all) constituted to be executed by a computer (for example, a specific module such as a software module can be provided which contains code which, when executed on the electronic processor of the computer, provides the data processing functionality of the respective method step). The method steps are executed for example by the processor of such a computer, for example by acquiring data sets at the processor and determining data sets by the processor.

For example, medical image data is acquired which describes (for example defines or represents) a digital medical image of an anatomical structure of a patient's body. The medical image data may have been generated by applying any kind of medical imaging modality (e.g. x-ray, computed x-ray tomography, magnetic resonance tomography, ultrasound imaging) to the anatomical structure. The anatomical structure can be any kind of anatomical structure, e.g. it can comprise at least one of hard (bony or cartilage) and soft (brain, skin or internal organ) tissue.

For example, image attribute data is acquired which describes (for example defines or represents) attribute information associated with the medical image data. The image attribute data can be embodied by metadata associated with the medical image data. The attribute information includes at least an indication of an initial reference system in which spatial relationships of the digital medical image are defined.

For example, positions in the digital medical image are defined in coordinates defined by the initial reference system. The indication of the initial reference system may be e.g. a version definition (version number) of the initial reference system or version definition (version number) of software used for generation (calculation) of the initial reference system. The attribute information in one example additionally describes at least one of generic descriptions of anatomy in the image, identifiers of content, or descriptors of pathological factors.

For example, reference system transformation data is acquired which describes (for example defines or represents) a spatial relationship between the initial reference system and a second reference system which is different from (i.e. not identical to) the initial reference system. The spatial relationship between the initial reference system and a second reference system can be defined by a transformation. Within the framework of this disclosure, a transformation can be embodied by a mapping such as a linear coordinate mapping, which can be represented by a transformation matrix (which in consequence can also be called mapping matrix) belonging to a for example linear mapping function. The transformation may have been determined (as part of the disclosed method or previously, before execution of the disclosed method is initiated) by execution of an image fusion algorithm (for example, an elastic fusion algorithm) to a positionally defined data set defining the initial reference system and a positionally defined data set defining the second reference system. Specifically, the reference system transformation data contains an indication between which individual reference systems the transformation establishes a mapping, for example the indication describes that the transformation maps between a specific first and another specific second version of an atlas. This allows determining the proper transformation among a potentially available plurality of transformation so that the correct mapping between the reference systems (atlas versions to be considered) can be selected and applied. Thereby, failure of the mapping algorithm (crashing the corresponding computer program) and/or wrong results can be avoided.

For example, transformed image data is determined based on (specifically, from) the medical image data and the reference system transformation data. The transformed image data describes (for example defines or represents) a representation of the digital medical image in the second reference system. Specifically, the transformed image data is determined by applying the transformation to the medical image data, thereby giving a definition of spatial relationships (such as positions) in the digital medical image in coordinates defined by the second reference system.

In a first example, the initial reference system and the second reference system are each defined by the coordinates of specific anatomical structures in the body of a first reference patient. In a second example, the initial reference system defines or is defined by the spatial relationships (specifically, absolute or relative positions, such as the positions of anatomical structures) in a first atlas.

Likewise, the second reference system can be defined by the spatial relationships (specifically, absolute or relative positions, such as the positions of anatomical structures) in a second atlas (irrespective of how the initial reference system is defined, i.e. irrespective of whether the initial reference system defines or is defined by the first reference patient or the first atlas), which second atlas is anyhow different from the first atlas. Alternatively, the second reference system may defined by the body of a second reference patient (irrespective of how the initial reference system is defined, i.e. irrespective of whether the initial reference system is defined by the first reference patient or the first atlas), which second reference patient is anyhow different from the first reference patient.

The second atlas may be a later version of the first atlas or a modification of the first atlas that describes a subvariant, for example an anatomical subvariant (e.g. the transformation of an atlas resulting from the image averaging of a young population data sample which is transformed to represent a suitable atlas for an older population by e.g. creating a subvariant with enlarged ventricles). The first atlas and the second atlas may differ in regard of at least one of patient population used for generating the atlas, spatial resolution, imaging modality used for generating the atlas, anatomical features included in the atlas, and pathological features included in the atlas.

The method disclosed method in one further example comprises optional steps relating to the generation of the reference system transformation data (specifically, of the spatial relationship spatial relationship between the initial reference system and a second reference system), which steps include:

acquiring, based on (specifically, via) the image attribute data, initial reference system data describing (for example, defining or representing) the geometry (specifically, positions or an algebraic basis) of the initial reference system (the initial reference system data may be stored separately and be found and loaded by the disclosed method using the information contained in the image attribute data as a pointer for finding the initial reference system data);

acquiring second reference system data describing (for example, defining or representing) the geometry (specifically, positions or an algebraic basis) of the second reference system different from the initial reference system;

determining, by the processor and based on the initial reference system data and the second reference system data, the reference system transformation data. The reference system transformation data is for example determined in the manner described above, such as by applying an image fusion algorithm to the initial reference system data and the second reference system data.

In a further example, at least part of the attribute information is defined in the initial reference system, for example spatial information contained in the attribute information such as a position of a specific body structure (e.g. a pathological structure such as an injury or a tumour) in the digital medical image. Them transformed attribute data may be determined based on (specifically, from) the image attribute data and the reference system transformation data, transformed attribute data describing a representation of attribute information associated with the medical image data in the second reference system. Spatial information describing e.g. the position of the specific body structure in the digital medical image may thereby be transformed into the second reference system.

Determining the transformed image data can have the effect of (and therefore comprise) compressing a plurality of image data sets (namely, multiple digital medical images belonging to different patients) into one medical image data set by generating a concise data set comprising the information about the spatial relationship between each patient-specific anatomical feature and the second reference system. Such compressing results in a data compression, for example a lossy data compression (i.e. a data compression which involves a loss of information of the compressed data compared to the input data/the data to be compressed). In any case, the data compression can be inverted to at least partially re-generate the image data based on the reference system transformation data, for example by applying the inverse of the above-described transformation.

In another aspect, the invention is directed to a computer program which, when running on a computer or when loaded onto a computer, causes the computer to perform the above-described method.

In a further aspect, the invention is directed to a non-transitory computer-readable program storage medium on which the aforementioned program is stored.

In an even further aspect, the invention is directed to a computer, for example a cloud computer, comprising a processor and a memory, wherein the aforementioned program is running on the processor or is loaded into the memory, or wherein the computer comprises the aforementioned program storage medium. The computer is for example an electronic data processing unit which is specifically configured to execute the aforementioned program, for example the electronic data processing unit of a medical navigation system or a medical procedure planning system (suitable for use e.g. in surgery or radiotherapy/radiosurgery or infusion therapy, for example for treating a brain tumour).

In an even further aspect, the invention relates to a (physical, for example electrical, for example technically generated) signal wave, for example a digital signal wave, carrying information which represents the aforementioned program, which comprises code means which are adapted to perform any or all of the method steps described herein.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

DEFINITIONS

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data, for example it encompasses the meaning of "inputting" or "loading" the data to be acquired, the expression "determining data" then encompasses the meaning of "outputting" the data to be determined. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. For example, the acquiring step does not involve an invasive step which would represent a substantial physical interference with the body, requiring professional medical expertise to be carried out and entailing a substantial health risk even when carried out with the required professional care and expertise. For example, the step of acquiring data, for example determining data, does not involve a surgical step and for example does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Atlas data describes (for example defines and/or represents and/or is) for example a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects. Anatomical structures are assigned grey values describing their response to at least one type of imaging radiation (such as their absorption of x-rays, defined for example in Hounsfield units). Thus, tissue types can be grouped into classes (so-called tissue classes) which define a specific type of tissue according to its physical properties such as absorption of the type of imaging radiation. The atlas can also be multi-modal, i.e. an atlas comprising tissue classes (tissue type information) which describes the image appearance of specific type of tissue in different imaging modalities, e.g. in x-ray-based imaging and magnetic resonance-based imaging, to allow matching the atlas with medical images having been generated by the corresponding imaging modality.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Within the framework of this disclosure, the term of transformation denotes a linear mapping (embodied for example by a matrix multiplication) defining an image fusion algorithm such as at least one of an elastic and an inelastic fusion transformation. Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, for example a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

DESCRIPTION OF THE FIGURES

In the following, the invention is described with reference to the appended figures which represent a specific embodiment of the invention. The scope of the invention is not however limited to the specific features disclosed in the context of the figures, wherein

As shown in FIG. 1, a patient image (called patient image v 1.0) which is defined in the initial reference system of a first version of an atlas (designated Atlas v 1.0) needs to be transferred into the second reference of a second version of the atlas (designated Atlas v 2.0), which constitutes an update of Atlas v 1.0. In order to do so, the spatial relationship between the initial reference system and the second reference system embodied by transformation REG between Atlas v 1.0 and Atlas v 2.0 is determined, e.g. as the result of applying an image fusion algorithm to Atlas v 1.0 and Atlas v 2.0. The reference system transformation data containing information characterising the transformation REG is supplied to a user (such as a healthcare facility) on a non-transitory computer-readable medium (such as a DVD or a flash memory device) e.g. together with the software update from Atlas v 1.0 to Atlas v 2.0. Alternatively, the transformation REG may be stored at a remote location, and the reference system transformation data may comprise a pointer to the storage location (e.g. on a cloud server) at which the transformation REG is stored and from which it may be loaded in order to be applied to the customer's patient image library. In doing so, the digital medical image embodied by patient image v 1.0 can be mapped into the second reference system by applying the transformation REG to patient image v 1.0 so as to determine patient image v 2.0 which constitutes the mapped digital medical image in the second reference system in which Atlas v. 2.0 is defined. Thereby, all images taken from different patients may be mapped into the second reference system to be as comparable to each other as before when they were all defined in the initial reference system of Atlas v 1.0.

FIG. 2 illustrates the case in which a user needs to update from Atlas v 1.0 directly to Atlas v 3.0 while omitting the intermediate update Atlas v 2.0, where Atlas v 2.0 constitutes an atlas version issued in between Atlas v 1.0 and Atlas v 3.0. The constituents of FIG. 1 which recur in FIG. 2 have the same meaning and functionality as explained with regard to FIG. 1. The case shown in FIG. 2 serves to illustrate as to why it useful that the attribute information contains information an indication of an initial reference system in which spatial relationships of the digital medical image are defined. In this case, even though Atlas v 2.0 is the update last issued, the transformation REG** between Atlas v 1.0 and Atlas v 3.0 needs to be applied to map the patient image v 1.0 into the second reference system represented by the reference system of Atlas v 3.0. A selection hence has to be made among the available transformations REG (between Atlas v 1.0 and Atlas v 2.0), REG* (between Atlas v 2. and Atlas v 3.0) and REG (between Atlas v 2.0 and Atlas v 3.0). By evaluating the indication of an initial reference system in which spatial relationships of the digital medical image are defined, which leads to the result that they are defined in the reference system of Atlas v 1.0, which leads the disclosed method to choosing REG as the transformation to be applied to update a library of digital medical images to the reference system of Atlas v 3.0. Thereby, the advantage is achieved that even users who did not apply all atlas updates in the past can use the disclosed method of automatic reference system update to keep the digital medical images contained in the library comparable to each other despite a changing atlas version.

Figure 1:
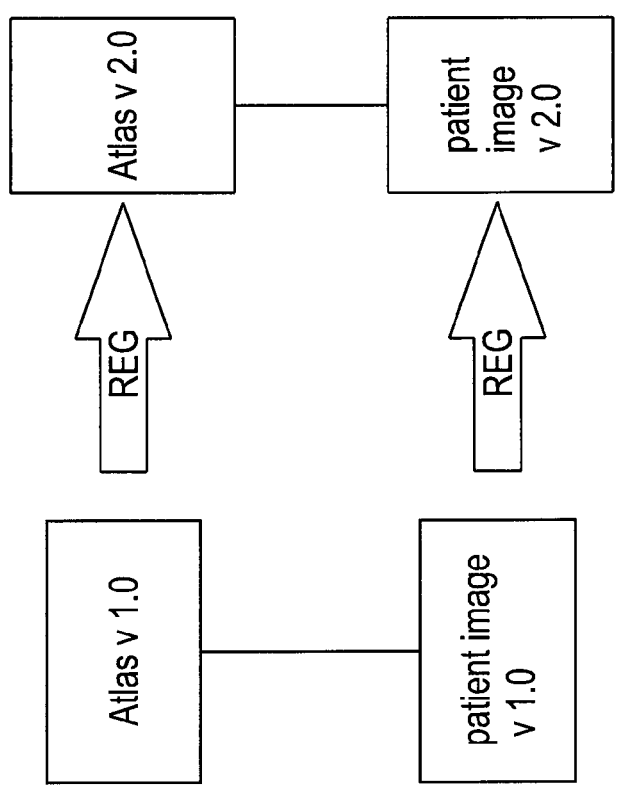
FIG. 1 is a block diagram illustrating the basic principle of the present (first) invention.
Figure 2:
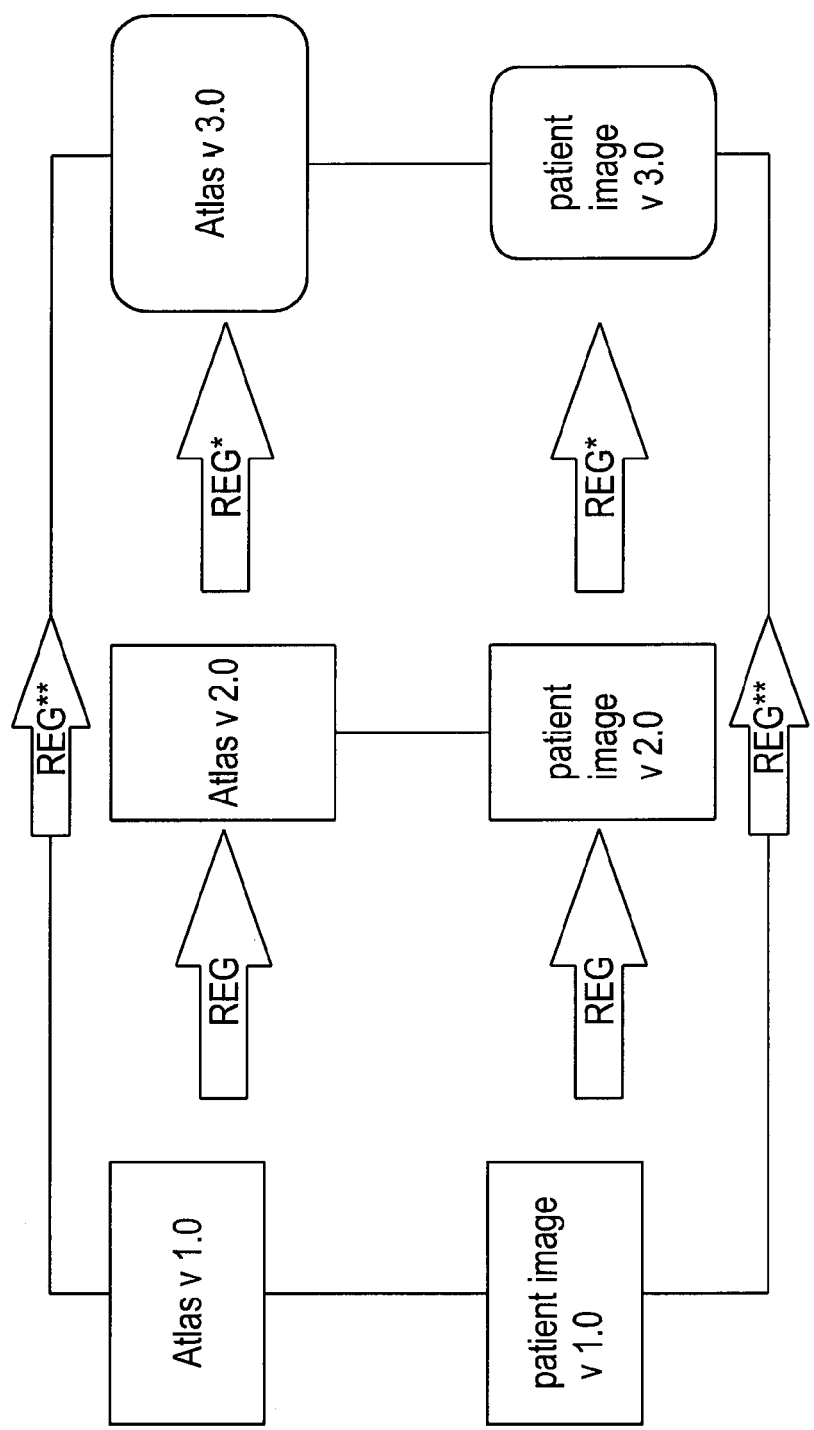
FIG. 2 is a block diagram illustrating application of the present (first) invention in case an intermediate atlas update has been omitted.

The disclosed method constitutes a proposal for digital signatures, references and pointers, data routing rules and update procedures that comprises the following exemplary features.

In a first example, all entities of Content_Com (for the meaning of abbreviations used hereinforth, reference is made to the introductory portion of the description) have to be signed with the attributes version of the common space (the atlas version), version of registration engine applied and unique identifier of the Registration used to transfer Content_Pat into said Content_Com.

In a second example, a central or group data aggregation scenario the administrative entity (for example, the supplier of the atlas software) has to provide a chain of Registrations connecting all versions of the common space up to the highest version in circulation within that exchange group.

In a third example, upon updates/upgrades of local versions of the Common Space (atlas) or registration engine, the most recent version of the chain of registrations between versions of the common space have to be dissemination along with the software update.

In a fourth example, each system applying some analysis to Content_Com needs to sign the result with unique identifiers listing all included (processed/analyzed) entities of Content_Com.

In a fifth example, aggregation and analysis systems have two parts, one that actively searches all patient files on the system for Content_Pat that is eligible to become Content_Com under a given semantic rule or analysis question and a second part the executes that operation upon request or automatically to generate a result, these two parts of such an operation can be scheduled/executed independently from one another.

In a sixth example, triggered or automatic dissemination of results onto known or new patients is the final step, such Content_Res needs to be signed with a unique identifier of the result (see the above fourth example) and as such with the version of the analysis engine and semantic context of the processing (essentially the question posed to the data).

In a seventh example, the dissemination system turning a result into Content_Res needs to have in-built similarity parameters that compare the patient (for whom Content_Res is applied) with the sample-history of the Result.

To the above first and second examples, the following applies: On that basis all Content_Com submitted into the group or central data repository can be migrated along the chain of known (high-quality) Registrations among versions of the Common Space and analysis (aggregation) can occur on the most recent version for all contents obtained.

To the above third example, the following applies: Upon update/upgrade of a single local system entity from one Common Space or registration engine to the next all localized Content_Com can be migrated along as well locally, so that local Content_Com is always stored in the most recent Common Space.

To the above fourth example, the following applies: On that basis the sample used to draw an inference (to generate a Result) can always be reconstructed and re-runs of the analysis can include data from different lists of submitted Content_Con (e.g. in the first analysis all data is considered, in the second invalid data is excluded or patients have withdrawn permission to use Contents derived from their data).

To the above fifth example, the following applies: With a system on that basis Content_Com can be theoretically deleted after production of a Result, since the Result contains all the required information to repeat drawing together all entities required to reproduce the input sample of the analysis, this saves storage space—alternatively all Content_Com files can be left intact, this saves analysis time for re-runs and allows theoretically for disconnection of the analysis system for the original patient files containing Content_Pat.

To the above sixth example, the following applies: On that basis Content_Res can be differentiated based on its origin, e.g. an image of the average location and volume of spleens drawn from a tumor patient population might be completely different to that drawn from a healthy population, by these signatures and references the history of Content_Res is available and false inferences from such information can be avoided even if the system should be disconnected from the level executing the analysis.

To the above seventh example, the following applies: Even before Content_Res is created (if that information is available) dissemination of non-applicable information can be avoided, one practical example would be an outcome map of surgical resection probability calculated from data from patients with low-grade glioma which shall not be applied (in which case Content_Res is not created) if a patient carries the disease classification high-grade Glioma, since it is not applicable and would mislead the practitioner. Alternatively, an alert can be displayed, so that the user can consciously choose to obtain Content_Res knowing it has limited applicability—this is an example of inference transparency in clinical decision support.

In the following, a further (second) invention is described with reference to FIG. 3.

Figure 3:
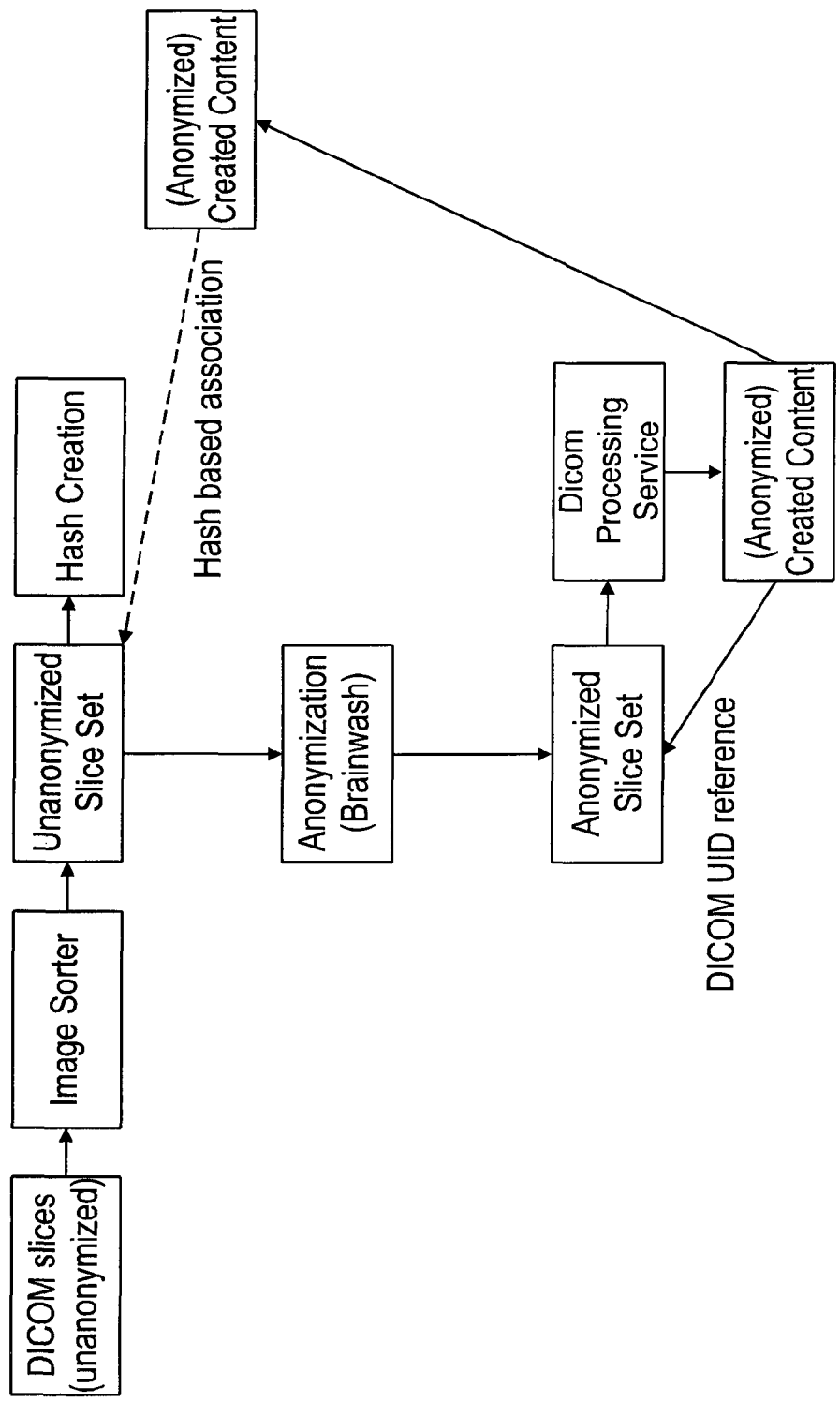
FIG. 3 is a block diagram illustrating a further (second) invention.

FIG. 3 constitutes a block diagram showing the connection of functional blocks corresponding to the following data processing for anonymising an image.

In a situation, where an initial medical patient image upload into the cloud occurs with anonymized data only there is no problem, because the processing can occur with the already anonymized data and the referencing of content and images is intact. However, images still have to be decrypted for the purpose of processing, which in this case is not a privacy, but an operational problem.

In a situation, where the initial image upload into the cloud occurs with unanonymised data but the user wishes processing, the problem is more complex since the processing entity can theoretically gain access to the personal health information enclosed in e.g. the DICOM tags of unanonymised DICOM data (digital image data in the format Digital Imaging and Communications in Medicine—DICOM).

One solution is to anonymize the DICOM data upon upload and store these anonymized (e.g. by applying Brainwash) copies in a processing entity in case processing is being triggered by the user. However, if the user wishes to see the results, the relationships have to be resolved via a referencing system that is a) not impacted by the anonymisation process (such as e.g. DICOM UIDs would be);
b) fast and reliable; and
c) does not rely on unanonymised patient data or some form of unified patient identifier connecting the anonymized and unanonymised contents.

Processing of anonymized DICOM images/slice sets in a DICOM processing service has the disadvantage that the contents derived from such images cannot be re-associated with the original unanonymised DICOM images/slice sets.

By calculating an image hash during the first image sorting procedure (when DICOM slices are "assembled" into a slice set) an image identifier is created that is not impacted by the anonymisation procedure (the included parts have to be chosen so that only tags are included that are not altered by anonymisation and anonymisation has to preserve pixel-values).

When processing has been completed on the anonymised data, the created content (objects from image segmentation, trajectories, landmarks etc.) references to that image hash instead of the DICOM UID.

On this basis the anonymized created content can be re-united with the unanonymised DICOM content (e.g. for the purpose of viewing) without unanonymised information having crossed the line between data storage and processing, while fully preserving the information on image-to-content or image-to-image relationships.

This second hash-based referencing system can rely on storing the hashes upon image sorting in a private tag, so that the point of hash creation can be either upon arrival in the cloud (after upload of single slices) or before upload (e.g. upon image sorting in a Quentry® desktop application as it is supplied by Brainlab AG).

The unanonymised DICOM slice sets can be stored in full encryption and only decrypted upon user access for sharing, viewing or editing. Only at this timepoint is the anonymized created content re-united with the unanonymised decrypted content via the image-hash based reference system. At this timepoint the hash-referencing can be resolved and replaced with the common DICOM UID (unique identifier) based referencing, e.g. prior to re-encryption before the user leaves the system.

In a further embodiment instead of utilizing the image hash atlas-based (e.g. Universal-Atlas-based) determined brain/anatomy properties can be utilized to generate a fingerprint of the individual in questions without the need to have a unified patient reference or personalized health information. In larger database applications a hash of that fingerprint can be also integrated to have perfect duplicate recognition and resolve patient-to-image relationships also.

In a further embodiment the anatomical fingerprint and the references of individual image hashes to it are stored to accommodate a use case, where anonymized data is added incrementally to a case file but the anonymisation is complete (no pseudonym or common case number is available). On the basis of anatomical fingerprinting re-association of the case files (DICOM) can be achieved without the necessity to perform actual re-identification of the patient.

By image hashing a digital signature of an image, an identifier can be created which is unique to the image. SHA-256 and MD5 are some of the most common algorithms for doing so. For illustration purposes one can e.g. think of the checksum (also called cross sum) of all pixel values in an image as a form of hash that is most likely unique to the image and allows re-identification of the image if it is not altered. As a nice side effect, it serves as a means of authentification to verify data integrity (is no image can be found with the hash reference content has been somehow altered through upload/processing/anonymisation in an undesired way).

Image-to-content and image-to-image relationships can be resolved for the purpose of anonymized DICOM image processing. Data privacy concerns for cloud based image processing architectures can be addressed.

The invention claimed is:

1. A computer-implemented method for determining a mapping of medical image content into a reference system, the method comprising executing, on at least one processor, steps of:
   acquiring, by the at least one processor, medical image data describing a digital medical image of an anatomical structure of a patient's body;
   acquiring, by the at least one processor, image attribute data describing attribute information associated with the medical image data, the attribute information including an indication of an initial reference system in which positions in the digital medical image are defined wherein the initial reference system is defined by the spatial relationships in a first atlas;
   acquiring, by the at least one processor, reference system transformation data describing a spatial relationship between the initial reference system and a second reference system which is different from the initial reference system wherein the second reference system is defined by the spatial relationships in a second atlas which is different from the first atlas;
   determining, by the at least one processor and based on the medical image data and the reference system transformation data, transformed image data describing a representation of the digital medical image in the second reference system;
   wherein the second atlas differs from the first atlas in regards to at least one of: patient population used for generating the atlas; spatial resolution; imaging modality used for generating the atlas; anatomical features included in the atlas; pathological features included in the atlas; is a modified representation of the first atlas or a modification of the first atlas that describes a subvariant.

2. The method according to claim 1, wherein the spatial relationship between the initial reference system and a second reference system is defined by a transformation, and wherein the transformed image data is determined by applying the transformation to the medical image data.

3. The method according to claim 2, wherein the transformation has been determined by execution of an image fusion algorithm.

4. The method according to claim 1, wherein the subvariant is an anatomical subvariant.

5. The method according to claim 1, wherein the first atlas and the second atlas differ in regard of at least one of patient population used for generating the atlas, spatial resolution, imaging modality used for generating the atlas, anatomical features included in the atlas, and pathological features included in the atlas.

6. The method according to claim 1, comprising:
   acquiring, by the at least one processor and based on the image attribute data, initial reference system data describing an algebraic basis of the initial reference system;
   acquiring, by the at least one processor, second reference system data describing an algebraic basis of the second reference system different from the initial reference system;
   determining, by the at least one processor and based on the initial reference system data and the second reference system data, the reference system transformation data.

7. The method according to claim 1, wherein at least part of the attribute information is defined in the initial reference system, the method further comprising:
   determining, by the at least one processor and based on the image attribute data and the reference system transformation data, transformed attribute data describing a representation of attribute information associated with the medical image data in the second reference system.

8. The method according to claim 1, wherein the attribute information describes at least one of generic descriptions of anatomy in the image, identifiers of content, or descriptors of pathological factors.

9. The method according to claim 1, wherein determining the transformed image data comprises compressing a plurality of image data sets into one.

10. A computer program which, when running on at least one processor of a computer or when loaded into the memory of a computer, causes the computer to perform the method according claim 1.

11. The method according to claim 10, wherein the compressing results in a data compression where the data compression can be inverted to at least partially re-generate the image data based on the reference system transformation data.

12. A non-transitory computer-readable program storage medium storing a plurality of instructions for determining a mapping of medical image content into a reference system, which when executed by at least one processor on a computer, causes the at least one processor to:
- acquire, by the at least one processor, medical image data describing a digital medical image of an anatomical structure of a patient's body;
- acquire, by the at least one processor, image attribute data describing attribute information associated with the medical image data, the attribute information including an indication of an initial reference system in which spatial relationships of the digital medical image are defined wherein the initial reference system is defined by the spatial relationships in a first atlas;
- acquire, by the at least one processor, reference system transformation data describing a spatial relationship between the initial reference system and a second reference system which is different from the initial reference system, wherein the second reference system is defined by the spatial relationships in a second atlas which is different from the first atlas;
- determine, by the at least one processor and based on the medical image data and the reference system transformation data, transformed image data describing a representation of the digital medical image in the second reference system;
- wherein the second atlas differs from the first atlas in regards to at least one of: patient population used for generating the atlas; spatial resolution; imaging modality used for generating the atlas; anatomical features included in the atlas; pathological features included in the atlas; is a modified representation of the first atlas or a modification of the first atlas that describes a subvariant.

13. A system for determining a mapping of medical image content into a reference system, the system comprising:
- at least one processor with associated memory, the memory storing instructions which, when executed by the at least one processor, cause the at least one processor to:
- acquire, by the at least one processor, medical image data describing a digital medical image of an anatomical structure of a patient's body;
- acquire, by the at least one processor, image attribute data describing attribute information associated with the medical image data, the attribute information including an indication of an initial reference system in which spatial relationships of the digital medical image are defined wherein the initial reference system is defined by the spatial relationships in a first atlas;
- acquire, by the at least one processor, reference system transformation data describing a spatial relationship between the initial reference system and a second reference system which is different from the initial reference system, wherein the second reference system is defined by the spatial relationships in a second atlas which is different from the first atlas;
- determine, by the at least one processor and based on the medical image data and the reference system transformation data, transformed image data describing a representation of the digital medical image in the second reference system;
- wherein the second atlas differs from the first atlas in regards to at least one of: patient population used for generating the atlas; spatial resolution; imaging modality used for generating the atlas; anatomical features included in the atlas; pathological features included in the atlas; is a later in time representation of the first atlas or a modification of the first atlas that describes a subvariant.

* * * * *